United States Patent [19]

Koropp

[11] Patent Number: 4,856,413

[45] Date of Patent: Aug. 15, 1989

[54] EXAMINATION APPARATUS WITH MASS BALANCING FOR A PART THEREOF WHICH IS PIVOTABLE ABOUT AN AXIS

[75] Inventor: Norbert Koropp, Reinbek, Fed. Rep. of Germany

[73] Assignee: U.S. Philips Corporation, New York, N.Y.

[21] Appl. No.: 274,714

[22] Filed: Nov. 17, 1988

Related U.S. Application Data

[63] Continuation of Ser. No. 499,622, May 31, 1983, abandoned.

[30] Foreign Application Priority Data

Apr. 6, 1982 [DE] Fed. Rep. of Germany ....... 3221043

[51] Int. Cl.[4] .............................................. F15B 11/08
[52] U.S. Cl. ........................................ 91/454; 91/471; 378/179
[58] Field of Search ...................... 378/179, 177, 175; 267/64.16; 280/DIG. 1; 91/390, 433, 454; 250/363 SC, 363 SF

[56] References Cited

U.S. PATENT DOCUMENTS 862,867   8/1907   Eggleston ........................ 417/390
2,828,139 3/1958   Lautzenhiser ............... 267/64.16 X
2,964,311 12/1960  Stelzer .............................. 267/64.16
3,260,164 7/1966   Guentner et al. ......................... 91/5
3,683,748 8/1972   Mahl et al. ........................... 91/416
3,894,476 7/1975   Cobb ................................... 91/390
4,233,516 11/1980  Trepte ................................ 250/444

FOREIGN PATENT DOCUMENTS 0535984 10/1931  Fed. Rep. of Germany .
2806956  8/1979  Fed. Rep. of Germany .
0969243  9/1964  United Kingdom .
1450473  9/1976  United Kingdom .
2014667  of 1979 United Kingdom .

Primary Examiner—Edward K. Look
Attorney, Agent, or Firm—Thomas A. Briody; Jack E. Haken; Jack D. Slobod

[57] ABSTRACT

The invention relates to an examination apparatus with a mass balancing device. The balancing device comprises a compressed air cylinder which operates as a gas pressure operated spring. The internal pressure of the cylinder can be controlled, by a pressure control circuit in dependence of the sine of the pivot angle. A pressure control circuit is a control signal supplied by a sine generator. The sine generator generates a signal which is dependent on the sine of the pivot angle.

9 Claims, 2 Drawing Sheets

4,856,413

EXAMINATION APPARATUS WITH MASS BALANCING FOR A PART THEREOF WHICH IS PIVOTABLE ABOUT AN AXIS

This is a continuation of application Ser. No. 499,622 filed May 31, 1983, now abandoned. Priority of application Ser. No. P3221043.4 filed on Apr. 6, 1982 in Fed. Rep. Germany, is claimed under 35 U.S.C. 119.

BACKGROUND OF THE INVENTION

The invention relates to an examination apparatus with a mass balancing device for a part of the apparatus which is pivotable about an axis. The mass balancing device comprises a compressed air cylinder which supports the pivotable apparatus part and in which a piston rod is slidably arranged. The compressed air cylinder comprises an opening for the inlet and outlet of air, and its internal pressure is controllable by means of a sine generator which generates a signal which corresponds to the sine of the pivot angle.

A device of this kind is known from U.K. patent application 2,014,667 (corresponding to German Auslegeschrift 2,806,956). This known device is also used for displacing the apparatus part, and its compressed air cylinder is divided into two chambers with different pressures. Each chamber comprises an opening through which air can be admitted or discharged, so that the apparatus part can be displaced in different directions. The required pneumatic control device is very complex and expensive. Once the compressed air source to which the compressed air cylinder is connected becomes defective, the apparatus part can no longer be displaced.

Furthermore, from U.S. Pat. No. 4,233,516 (corresponding to German Auslegeschrift 2,557,810) a stand is known for an X-ray image forming device in which a displaceable apparatus part is supported by a gas-pressure operated spring. Even though mass balancing in this device is substantially simpler than in the previously described device, the apparatus part can be displaced only in the vertical direction.

SUMMARY OF THE INVENTION

It is an object of the invention to provide a simply constructed device for displacing a pivotable apparatus part in different directions according to which the position of the examination apparatus whereto it is connected.

This object is achieved according to the invention in a device in which the piston is arranged and constructed so that the pressure is homogeneously distributed throughout the compressed air cylinder. A pressure control circuit is provided for which the control signal is supplied by the sine generator.

In cooperation with the control circuit which is controlled by the sine generator, the compressed air cylinder acts as a gas-pressure operated spring whose gas pressure is varied according to the relevant position of the X-ray examination apparatus. As a result the forces exerted on the piston by the gas pressure in the cylinder and by the apparatus part are equal in each position of the apparatus part so that the weight of the apparatus part is balanced.

In a further embodiment of the invention, there is provided a measuring element for measuring the force exerted on the apparatus part by the operator. The output signal of the measuring element is superposed on the control signal.

Thus, a servo drive is obtained in which the gas pressure, and hence the force acting on piston and on the apparatus part, corresponds to the force exerted by the operator.

In a further embodiment according to the invention, the control circuit comprises a valve device which is coupled to the compressed air cylinder. The valve device has one valve for admitting air to the cylinder and one valve for discharging air from the cylinder. Each of the valves is activatable by a motor. A spring is coupled to each motor and the associated valve so that it is tensioned when the valve is opened by the motor.

Should the associated motor become defective in the open position of a valve, for example, due to a power failure, the relevant valve will be closed by the spring so that the pressure in the compressed air cylinder is substantially sustained.

DESCRIPTION OF THE PREFERRED EMBODIMENTS

Figure 1:
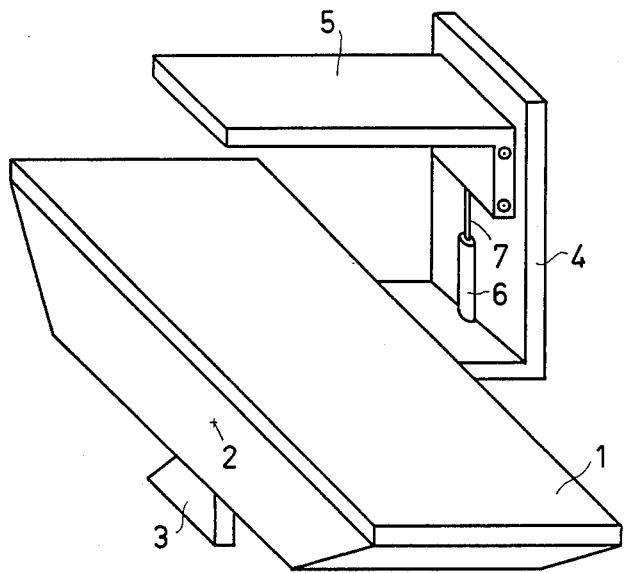
FIG. 1 schematically shows an X-ray examination apparatus according to the invention comprising a compressed air cylinder.

The X-ray examination apparatus shown in FIG. 1 comprises a frame 1 with a patient support table which is pivotable about a horizontal axis 2 at the base 3 of the apparatus. Inside the frame 1 a longitudinal carriage 4 can be displaced in a plane parallel to the plane of the patient support table. A carriage 5, which supports a spot film device, is displaceable perpendicularly to the support table in guide rails (not shown) on the frame 1.

Figure 2:
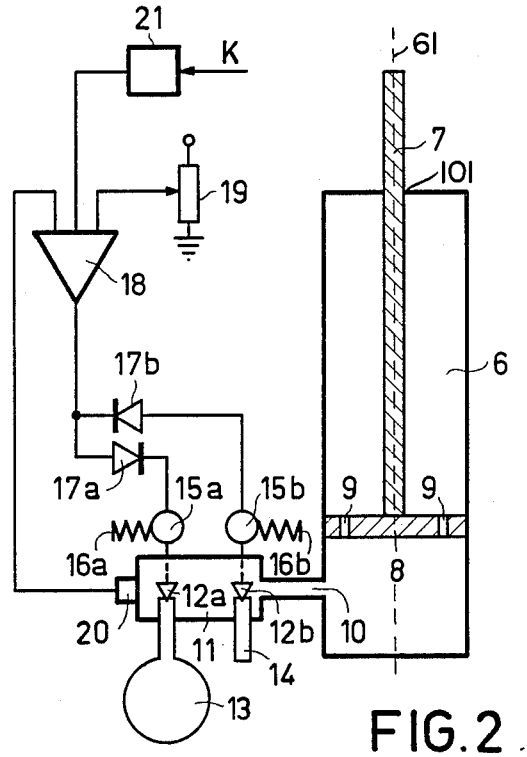
FIG. 2 schematically shows a block diagram of the cylinder of FIG. 1.

Connected to the longitudinal carriage 4 is a compressed air cylinder 6 having an axis 61 (FIG. 2). In cylinder 6 a piston 7 is arranged so as to be displaceable. One of the piston is connected to the carriage 5. The pressure in the piston is always varied so that the weight of the spot film device on carriage 5 is balanced.

When the X-ray examination is horizontal the pressure in the piston must reach a maximum value so that the force acting on the piston corresponds to the weight of the spot film device. When the X-ray examination apparatus is vertical, however, no force need be exerted on the piston.

As appears from FIG. 2 a guide flange 8 is connected to the part of piston 7 which projects into the cylinder through opening 101. Piston 7 is arranged to fit closely in opening 101 to minimize air leakage through the opening. The flange 8 comprises bores 9 through which gas or air can flow between the parts of the compressed air cylinder 6 which are separated by the guide flange 8. Consequently, the air pressure is the same throughout the compressed air cylinder 6. The force exerted by the air pressure on the piston 7 corresponds to the cross-sectional area of the piston 7 multiplied by the pressure prevailing in the cylinder.

Via an opening 10, the compressed air cylinder communicates with a valve device 11. Valve device 11 comprises two valves 12a and 12b. When the valve 12a is opened, air flows into the cylinder 6 from a compressed air source 13 in which air is stored with a pressure which is substantially higher than the highest pressure required in the compressed air cylinder 6. The pressure in the cylinder is thus increased. However, when the valve 12b is opened, air flows from the compressed air cylinder 6 to the environment via a duct 14. In order to prevent noise, a silencer may be connected to the duct 14.

The positions of the valves 12a and 12b are determined by motors 15a and 15b, respectively. The motors are capable of opening the associated valves against the force of a spring 16a or 16b, respectively.

One terminal of each motor 15a and 15b is connected to the output of an amplifier 18 via diodes 17a and 17b. Diodes 17a and 17b have opposed forward directions. Their other terminals are connected to a potential which corresponds to the rest potential, that is to say the potential on the output of the amplifier 18 in the absence of an input signal.

The tap of a sine potentiometer 19 is connected to the input of the amplifier 18. The potentiometer is connected to the frame 1 of the examination apparatus so that the voltage on the tap varies sinusoidally with the pivot angle of the examination apparatus. Consequently, the voltage on this tap corresponds to the force exerted on the piston 7 by the spot film carriage 5 in each position of the apparatus. This force may be up to 2000N when the examination apparatus is horizontal.

A pressure sensor 20, which supplies a signal which is proportional to the pressure in the compressed air cylinder 6 is connected to the other input of the amplifier 18. The amplifier 18 forms a signal which corresponds to the difference between these two signals (the force signal and the pressure signal) so that the potential on the output of the amplifier 18 becomes negative when the signal supplied by the pressure sensor 20 is larger than the signal on the tap of the sine potentiometer 19. The potential on the output of the amplifier 18 becomes more positive when the signal supplied by the pressure sensor 20 is smaller than the signal derived from the tap of the sine potentiometer.

Consequently, when the pressure in the cylinder 6 becomes too high, the diode 17b becomes conductive so that the motor 15b is activated. Motor 15b opens the valve 12b with the result that air is discharged and the pressure in cylinder 6 decreases. The motor 15b at the same time tensions the spring 16b. When the pressure in the cylinder 6 has decreased so far that the signal supplied by the pressure sensor 20 corresponds to the voltage on the tap of the sine potentiometer, the diode 17b is blocked. The valve 12b is then closed by the spring 16b tensioned by the motor 15b, and the pressure remains constant.

When the pressure in the compressed air cylinder is lower than the value corresponding to the voltage on the potentiometer tap (this may occur, for example, when the X-ray examination apparatus is pivoted to a horizontal position), the potential on the output of the amplifier 18 becomes more positive so that the diode 17a becomes conductive and the motor 15a is activated. Motor 15a opens the valve 12a and the spring 16a is tensioned. Air then flows from the compressed air source 13 to the compressed air cylinder 6 until the pressure therein becomes so high that the voltages on the outputs of the elements 19 and 20 are the same. Subsequently, the voltage to the motor 1a is switched off again, after which the valve 12a is closed again by the spring 16a.

Thus, a control circuit is obtained whose control variable or control signal is the voltage on the tap of the sine potentiometer 19. By suitable attenuation or amplification of the signals supplied by the pressure sensor 20 and/or the sine potentiometer 19, the force exerted on the piston 7 by the compressed air inside the compressed air cylinder 6 can be made exactly equal to the force exerted on the piston by the apparatus part for each position of the X-ray apparatus. Mass balancing without a counterweight is thus achieved.

The operator can in principle displace the apparatus part by hand because only the acceleration and frictional forces have to be overcome to displace the apparatus part. However, displacement of the spot film device by servo motor control can also be readily achieved. The force exerted by the operator may then be smaller than required for acceleration of the apparatus part and for overcoming the friction.

To this end, there is provided a transducer 21 (FIG. 2) which converts the force exerted on the apparatus part by the operator, for example, on a grip, into an electric signal. The electrical signal is applied to an input of the amplifier 18 on which the force signal supplied by the sine potentiometer 19 is superposed. As a result, the pressure in the compressed air cylinder 6 increases or decreases according to the direction of the force acting on the apparatus part. When the ratio between the force K measured by the transducer 21 and exerted by the operator and the electric signal produced by the transducer 21 is constant and independent of the force, a pressure variation is produced in the compressed air cylinder 6. The pressure variation is proportional to the force, so that the piston 7 is moved up or down with a force which is proportional to (but larger than) the force exerted by the operator. Consequently, the effort required by the operator is reduced.

Figure 3:
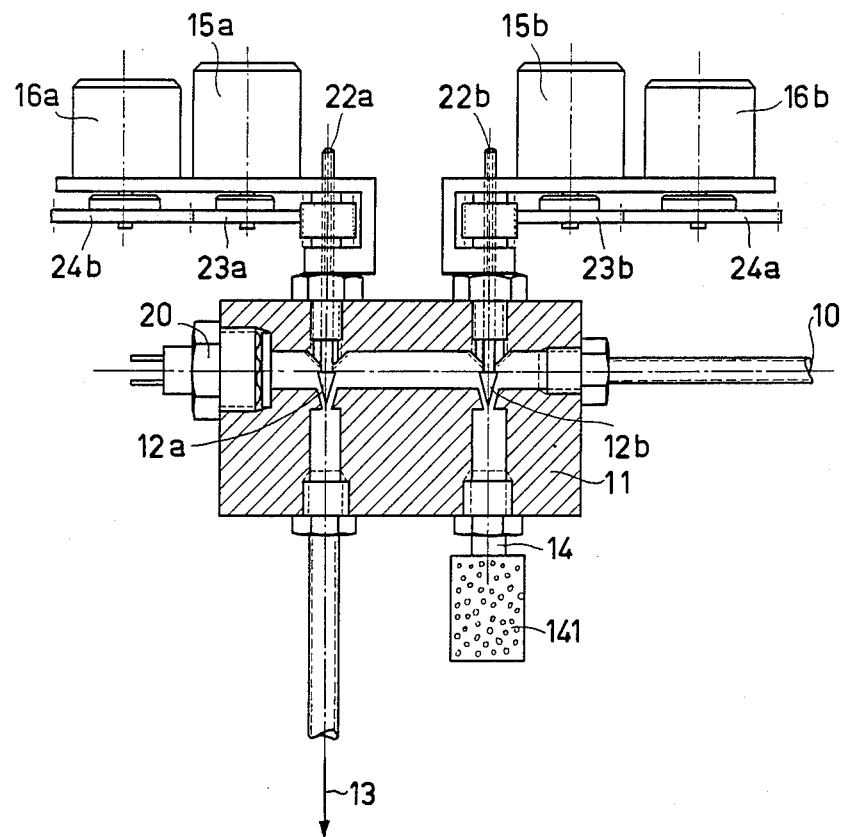
FIG. 3 schematically shows an adjusting element included in a control circuit.

As appears from FIG. 3, the valve device 11 comprises two valves 12a and 12b. Each valve has a conical shape. The valves can be pressed into or out of conical valve seats by means of a spindles 22a and 22b, respectively. Spindles 22a and 22b are coupled to motors 15a and 15b, respectively, via pinions 23a and 23b, respectively.

The springs 16a and 16b are coupled to the pinions 24b and 24a, respectively, so that when the valve is opened by the motor, the tensioned spring is further tensioned. When the desired pressure is reached so that the output signal of the amplifier 18 is zero, or in the case of a power failure, the springs 16a and 16b immediately close the associated valves, should they still be open. The pressure in the compressed air cylinder 6 is then sustained, even when there is a power failure, because it is substantially independent of the position of the piston 7. (This is because the volume of air displaced by piston 7 is small in comparison with the total volume of the cylinder 6. The force exerted on the piston therefore remains substantially constant regardless of its position.) Consequently, in the case of, for example, a power failure, the apparatus part can still be readily moved so long as the examination apparatus remains in its angular position.

What is claimed is:

1. An examination apparatus comprising:
   an examination table for supporting a patient;
   means for examining the patient supported on the examination table; and
   a mass balancing device for supporting the examining means over the patient on the table, said table, examining means, and balancing device forming an assembly which is pivotable about a horizontal axis;

characterized in that the mass balancing device comprises:

an air cylinder connected to the examination table, said air cylinder having an axis, at least one side wall parallel to the axis, a cross-section perpendicular to the axis, and an end wall with an opening;

a piston having two ends, one end connected to the examining means and the other end arranged in the cylinder, said piston being slidably arranged to fit closely in the opening in the end wall of the cylinder to slide parallel to the cylinder axis, said piston having a cross-section perpendicular to the axis which is less than the cross-section of the cylinder;

a guide flange connected to the end of the piston in the cylinder, said guide flange bearing on the side wall of the cylinder and separating the cylinder into two parts, said guide flange having at least one bore therein through which air can flow between the two parts of the cylinder separated by the guide flange;

a potentiometer having a tap, said potentiometer producing a signal at the tap whose voltage represents the sine of the pivot angle of the assembly about the horizontal axis;

a pressure sensor for generating a pressure signal representing the air pressure in the cylinder;

a first electrically-controlled valve, spring biased to close in the absence of the application of an electrical activation signal thereto;

a compressed air source for storing air at a pressure substantially higher than that needed in the air cylinder, said air source pneumatically communicating with the air cylinder via the first valve;

a second electrically-controlled valve, spring biased to close in the absence of the application of an electrical activation signal thereto, said valve forming pneumatic communication between the air cylinder and its external environment when the second valve is open;

a control circuit having two inputs and two outputs, one input receiving the pivot angle signal and the other input receiving the pressure signal, one output providing an electrical activation signal to the first valve when the pivot angle signal exceeds the pressure signal, the other output providing an electrical activation signal to the second valve when the pressure signal exceeds the pivot angle signal.

2. In an examination apparatus having two parts which are displaceable toward or away from each other along a displacement axis substantially perpendicular to a plane containing a pivot axis about which said two parts pivot as a unit, thereby varying the angular position of said displacement axis about said pivot axis, the mass balancing device for maintaining relative support between said parts comprising:

an air cylinder acting between said two parts, said air cylinder having two opposed working chambers and an opening communicating between the chambers to give spring characteristics to said cylinder;

means responsive to the angular position of said displacement axis about said pivot axis for generating a first signal representing the required air pressure in said cylinder to produce a force balancing the component of the gravitational force acting on one of said parts along said displacement axis; and control means for selectively supplying pressured air to or venting pressurized air from the cylinder, said control means comprising:

means for generating a second signal representing the actual air pressure in said cylinder;

means for comparing the said first and second signals; and means for varying the air pressure in the cylinder in response to the difference between said first and second signals.

3. The apparatus of claim 2, further comprising operator control means for generating a third pressure signal representing the force which an operator selectively directs be applied between said parts to selectively move said parts away from or toward each other along said displacement axis, said control means being responsive to the combination of said first and third signals, said comparing means comprising means for comparing the combination of said first and third signals with said second signal, and said varying means being responsive to the difference between the second signal and the combination of said first and third signals.

4. The apparatus of claim 3, wherein said varying means comprises first valve means for supplying air pressure to the cylinder in response to the combination of said first and third signals exceeding said second signal and second valve means for venting air pressure from the cylinder in response to said second signal exceeding the combination of said first and third signals.

5. The apparatus of claim 4, wherein said means responsive to the angular position of said displacement axis about said pivot axis generates said first signal in proportion to the sine of the angle between said displacement axis and the horizontal.

6. The apparatus of claim 3, wherein said means responsive to the angular position of said displacement axis about said pivot axis generates said first signal in proportion to the sine of the angle between said displacement axis and the horizontal.

7. The apparatus of claim 2, wherein said varying means comprises first valve means for supplying air pressure to the cylinder in response to said first signal exceeding said second signal and second valve means for venting air pressure from the cylinder in response to said second signal exceeding said first signal.

8. The apparatus of claim 7, wherein said means responsive to the angular position of said displacement axis about said pivot axis generates said first signal in proportion to the sine of the angle between said displacement axis and the horizontal.

9. The apparatus of claim 2, wherein said means responsive to the angular position of said displacement axis about said pivot axis generates said first signal in proportion to the sine of the angle between said displacement axis and the horizontal.

* * * * *